United States Patent
Klopprogge et al.

(10) Patent No.: US 7,192,749 B2
(45) Date of Patent: Mar. 20, 2007

(54) **USE OF THE REPRESSOR GLXR FOR THE SYNTHESIS OF LYSINE IN *CORYNEBACTERIUM GLUTAMICUM***

(75) Inventors: Corinna Klopprogge, Mannheim (DE); Oskar Zelder, Speyer (DE); Burkhard Kröger, Limburgerhof (DE); Hartwig Schröder, Nussloch (DE); Stefan Häfner, Ludwigshafen (DE); Heung-Shick Lee, Seoul (KR)

(73) Assignee: BASF Aktiengesellschaft (DE)

( * ) Notice: Subject to any disclaimer, the term of this patent is extended or adjusted under 35 U.S.C. 154(b) by 0 days.

(21) Appl. No.: 10/514,076

(22) PCT Filed: May 13, 2003

(86) PCT No.: PCT/EP03/04969

§ 371 (c)(1),
(2), (4) Date: Nov. 11, 2004

(87) PCT Pub. No.: WO03/097678

PCT Pub. Date: Nov. 27, 2003

(65) Prior Publication Data

US 2005/0196847 A1 Sep. 8, 2005

(30) Foreign Application Priority Data

May 16, 2002 (EP) .................... 02010924

(51) Int. Cl.
| | |
|---|---|
| *C12P 13/08* | (2006.01) |
| *C12P 21/06* | (2006.01) |
| *C12N 1/21* | (2006.01) |
| *C12N 15/17* | (2006.01) |
| *C12N 9/10* | (2006.01) |
| *C07H 21/02* | (2006.01) |
| *C12H 21/04* | (2006.01) |

(52) U.S. Cl. ................ 435/115; 435/252.32; 435/69.1; 435/320.1; 435/193; 536/23.2

(58) Field of Classification Search ............... 435/23.1, 435/115
See application file for complete search history.

(56) References Cited

FOREIGN PATENT DOCUMENTS

| EP | 1 108 790 A2 | 6/2001 |
|---|---|---|
| EP | 1 362 866 A1 | 11/2003 |

OTHER PUBLICATIONS

Chung T, et al. Glyoxylate bypass operon of *Escherichia coli*: cloning and determination of the functional map. J Bacteriol. Jan. 1988;170(1):386-92.
Database Accession No. AX123710. Novel Polypeptides. May 10, 2001.
Database Accession No. BD571237. Novel Polynucleotides. Jan. 17, 2003.
Database Accession No. AF293334. Probable Transcription Regulator. Jun. 8, 2001.
Database Accession No. Q8FTU1. The entire genomic sequence of *Corynebacterium efficiens* YS-314. Mar. 1, 2003.
Database Accession No. AB083047. drp86 of *Corynebacterium glutamicum*. Apr. 3, 2002.
Database Accession No. AAG90072. Sep. 26, 2001.
Kim, et al. Utilization of LACZ to isolate regulatory genes from *Corynebacterium glutamicum*. Journal of Microbiology & Biotechnology. Apr. 2002. 12(2):336-339.
Lee, et al. Molecular Characterization of AceB, a gene encoding malate synthase in *Corynebacterium glutamicum*. Journal of Microbiology & Biotechnology. 1994 4(4):256-263.
Reinscheid, et al. Characterization of the isocitrate lyase gene from *Corynebacterium glutamicum* and biochemical analysis of the enzyme. J Bacteriol. Jun. 1994;176(12):3474-83.
Sunnarborg, et al. Regulation of the glyoxylate bypass operon: cloning and characterization of iclR. J Bacteriol. May 1990;172(5):2642-9.
Wendisch VF, et al. Regulation of acetate metabolism in *Corynebacterium glutamicum*: transcriptional control of the isocitrate lyase and malate synthase genes. Arch Microbiol. Oct. 1997;168(4):262-9.
International Search Report for PCT/EP03/04969 Mailed Jan. 24, 2004.

*Primary Examiner*—Ponnathapu Achusamurthy
*Assistant Examiner*—Iqbal Chowdhury
(74) *Attorney, Agent, or Firm*—Lahive & Cockfield, LLP; Elizabeth A. Hanley; Maria Laccotripe Zacharakis (57) ABSTRACT

Isolated polypeptide sequence having the sequence of SEQ ID NO:1 or muteins thereof having the ability to bind cAMP and repress the expression of the aceB gene of *C. glutamicum* and which can be obtained from SEQ ID NO:1 by inserting, deleting or substituting up to 20% of the amino acids.

13 Claims, 7 Drawing Sheets

```
                                                                                              50
         10              20              30            40            50
CG :  VEGVQEILSRAGIFQGVDPTAVNNLIQDMETVRIRGATIFDWICPGDRL :        50
MT :  MD---EILARAGIFQGVEPSAIAALTKQLQPVDLRGHTVFAHGPGDRL :        47
SC :  MD---DVLRRNPLFAALDDEQSAELRASMSEVTLARGDTLFHLGPGDRL :       47
VC :  M------VLGKPQTDPTLE----WFLSHCHIHKTSIHAGLKAETL :            40
EC :  M------VLGKPQTDPTLE----WFLSHCHIHKVSKSTLIRGLKAETL :         40

60              70              80            90            100
CG :  YIITSGKVKLARHAPDGRENLLIMGPSEMEGELSIFDPGP-RISSAVCV :       99
MT :  YIIH-SGKVKIGRRAPDGRENLLIMGPSEMEGELSIFDPGP-RISSATTI :      96
SC :  YVVTEGKVKLHRTSPDGRENMIAVVGPSELIGELSLFDPGP-RTATGTAL :      96
VC :  YYIVKGSVAVLIKDEEGKEMILSYLNQGIFIGELGFEEGQERTAWVRAK :       90
EC :  YYIVKGSVAVLIKDEEGKEMILYYLNQGLFIGELGLEEGQERSAWVRAK :       90

Cyclic nucleotide-monophosphate binding domain
        110             120             130           140           150
CG :  TEVHAATMNSDMLRNWADHPATAEQLLRVARRLRRTNASIADLIFTDV :        149
MT :  TEVRAVSMDRDALRSWIADRPEISEQLLRVLARRLRRTNNNLADLIFTDV :      146
SC :  TEVKLLALGHGDLQPWENVRPEVATALLRAVARRLRKTNDAMSDIVFSDV :      146
VC :  TPCEVAEISFKKFRQLIQVNPDILMRESGQMARRIQVTSQKVGDLAFLDV :      140
EC :  TACEVAELSYKKFRQLIQVNPDILMRESAQMARRIQVTSEKVGNLAFLDV :      140

160             170             180           190           200
CG :  PGRVAKTLIQLLNRFGTQEA-GALRVNHDLTQEEIAQLVGASRETVNKAL :       198
MT :  PGRVAKQLIQLLQRFGTQEG-GALRVTHDLTQEEIAQLVGASRETVNKAL :       195
SC :  PGRVARALDLSRRFGVQSE-EGIHVTHDLTQEBLAQLVGASRETVNKAL :        195
VC :  TGRIAQTHNLIRQPDAMTHPDGMQI--KITRQEIGIQIVGCSRETVGRIL :       188
EC :  TGRIAQTHNLIKQPDAMTHPDGMQI--KITRQEIGIQIVGCSRETVGRIL :       188

Helix-Turn-Helix DNA binding motif
        210             220             230
CG :  ATFAHRGWIRLEEKSVLIVDTEHLARRARV :                            228
MT :  ADFAHRGWIRLECKSVLISDERLARRAR- :                             224
SC :  ADFAQRGWLRLEARAVILLLDVERLAKRSR- :                           224
VC :  KMLEEQNLISAHGKNIIVVYGR------- :                             210
EC :  KMLEDQNLISAHGKNIIVVYGR------- :                             210
```

USE OF THE REPRESSOR GLXR FOR THE SYNTHESIS OF LYSINE IN *CORYNEBACTERIUM GLUTAMICUM*

*Corynebacterium glutamicum* is a gram-positiv organism and has been well known as the host organism for the industrial production of amino acids, such as glutamate and lysine [Kinoshita, 1995]. Due to the role of the organism in amino acid production, the catabolic and anabolic pathways leading to the industrially important amino acids have been studied in detail during the past decades [for review see Sahm et al, 1995; Malumbres and Martin, 1996]. Although necessary for the in-depth understanding of the metabolic pathways, the information on the regulatory mechanism of gene expression in the organism is very limited.

Figure 1:
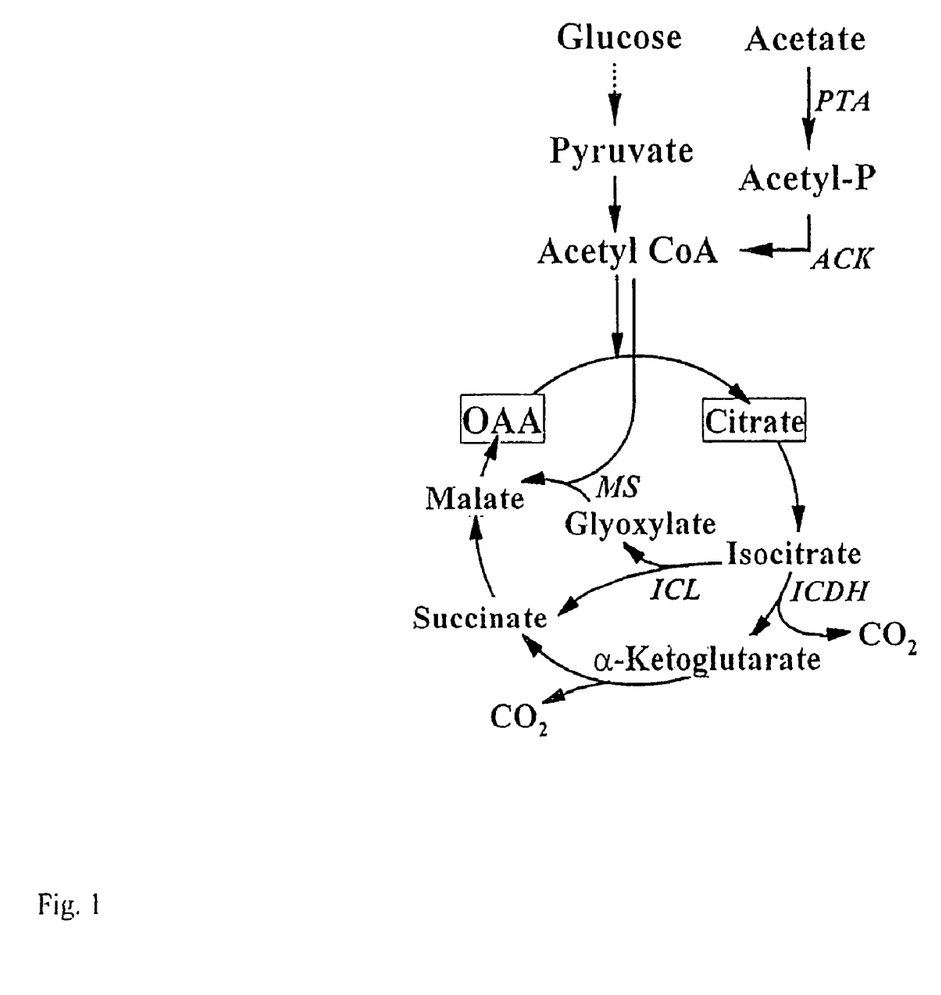

The glyoxylate bypass of *C. glutamicum* is a good candidate for studying the regulatory mechanism of gene expression, because the expression of the isocitrate lyase and malate synthase, which catalyze the bypass (FIG. 1), is tightly regulated by the availability of carbon sources [Wendisch et al, 1997].

The isocitrate lyase encoded by the aceA gene catalyzes the conversion of the TCA intermediate, isocitrate, into glyoxylate and succinate [Reinscheid et al, 1994a]. The malate synthase encoded by the aceB gene catalyzes subsequent condensation of glyoxylate with acetyl-CoA to produce malate, which in turn enters the TCA cycle [Lee and Sinskey, 1994; Reinscheid et al, 1994b]. The aceA and aceB genes are derepressed by two-carbon compounds, such as acetate provided as the sole source of carbon, conserving the acetate carbon for the biosynthesis of cell material by bypassing the $CO_2$-generating steps of the TCA cycle. Glucose, supplied as a carbon source, represses the aceA and aceB genes. The expression of the glyoxylate bypass enzymes is regulated at the level of transcription by the available carbon sources [Wendisch et al, 1997], but the mechanism of transcriptional regulation is largely unknown, although Wendisch et al suggested the involvement of acetyl-CoA as the signaling molecule [Wendisch et al, 1997]. In *Escherichia coli*, the IclR repressor is known to be responsible for the regulation of the aceBAK operon [Chung et al, 1988; Sunnarborg et al, 1990]. The expression of iclR is regulated by FadR which is known to regulate the expression of the genes involved in the fatty acid metabolism. Although the structural organization of the aceA and aceB genes in *C. glutamicum* is different from that of *E. coli*, the regulation of gene expression by the available carbon sources appear to have common features.

SUMMARY OF THE INVENTION

The present invention provides novel polypeptide molecules which have the ability to repress the gene expression of at least the aceB gene of *Corynebacterium glutamicum*. These molecules are referred to as glxR molecules (glyoxylate bypass regulators). Another aspect of the invention relates to polynucleotide sequences which code for the above-mentioned glxR molecules. Another aspect of the invention relates to the use of glxR molecules for influencing the synthesis of amino acids in hosts such as *Corynebacteria*.

DETAILED DESCRIPTION OF THE INVENTION

The present invention provides novel polypeptide molecules which have the ability to repress the gene expression of at least the aceB gene of *Corynebacterium glutamicum*.

The isolation of the glxR molecule having the polypeptide sequence depicted in SEQ ID NO:1 is described in the experimental section.

The preparation of glxR muteins, having the ability to bind cAMP and repress the transcription of the aceB gene coding for malat synthase of *C. glutamicum* is described in the experimental section.

Polynucleotide sequences encoding the glxR molecules and glxR muteins can be prepared by back-translation of the respective polypeptide sequences according to the genetic code and chemical synthesis of said polynucleotide sequences. The isolation of the polynucleotide sequence encoding the glxR molecule according to SEQ ID NO:1 is described in the experimental section.

Another aspect of the invention is the use of the glxR molecules and the respective polynucleotide sequences for modulating at least the expression of the aceB gene of *C. glutamicum*. In one embodiment a polynucleotide sequence encoding a glxR molecule is recombinantly introduced in a host organism of the genus *Corynebacterium* which has a functional aceB gene. At least the gene expression of this aceB gene is modulated on the transcriptional level compared to the naturally occuring genome organization of *Corynebacteria*. By expressing the glxR molecules in an amount distinctly higher as the naturally occurring amount, a more effective gene repression of aceB is effected.

In another embodiment of the invention an antisense molecule to the polynucleotide sequence encoding a glxR molecule is introduced to a host organism. This antisense molecule reduces the expression of the glxR gene and effects an amount of glxR molecules in the host which is lower than the naturally occuring amount. This results in a higher transcription rate of the aceB gene.

In another embodiment of the invention the polynucleotide sequence encoding a glxR molecule is deleted partially or completely in the host organism. This results in a higher transcription rate of the aceB gene.

By modulation of the aceB gene expression the glyoxylate bypass is influenced directly. The modulation can be in both directions i.e. up-regulation and down-regulation. By influencing the glyoxylate bypass the metabolic flux of amino acids and intermediates thereof can be influenced effectively in *Corynebacterium*.

As *Corynebacterium* is used as an organism for the production of amino acids, preferably of lysine, glutamate and methionine, the influence on the glyoxylate bypass via the glxR molecules can be used to shift the production of amino acids in *Corynebacterium*. In some cases it will be advantageous to shift production of the desired amino acid to higher amounts whereas in some other cases a shift in the opposite direction is desired, e.g. in order to block the synthesis of unwanted intermediates.

The influence of the glyoxylate bypass by the glxR molecules is an effective way to design the metabolic capacity of *Corynebacteria*.

Experimental Section

Figure 2:
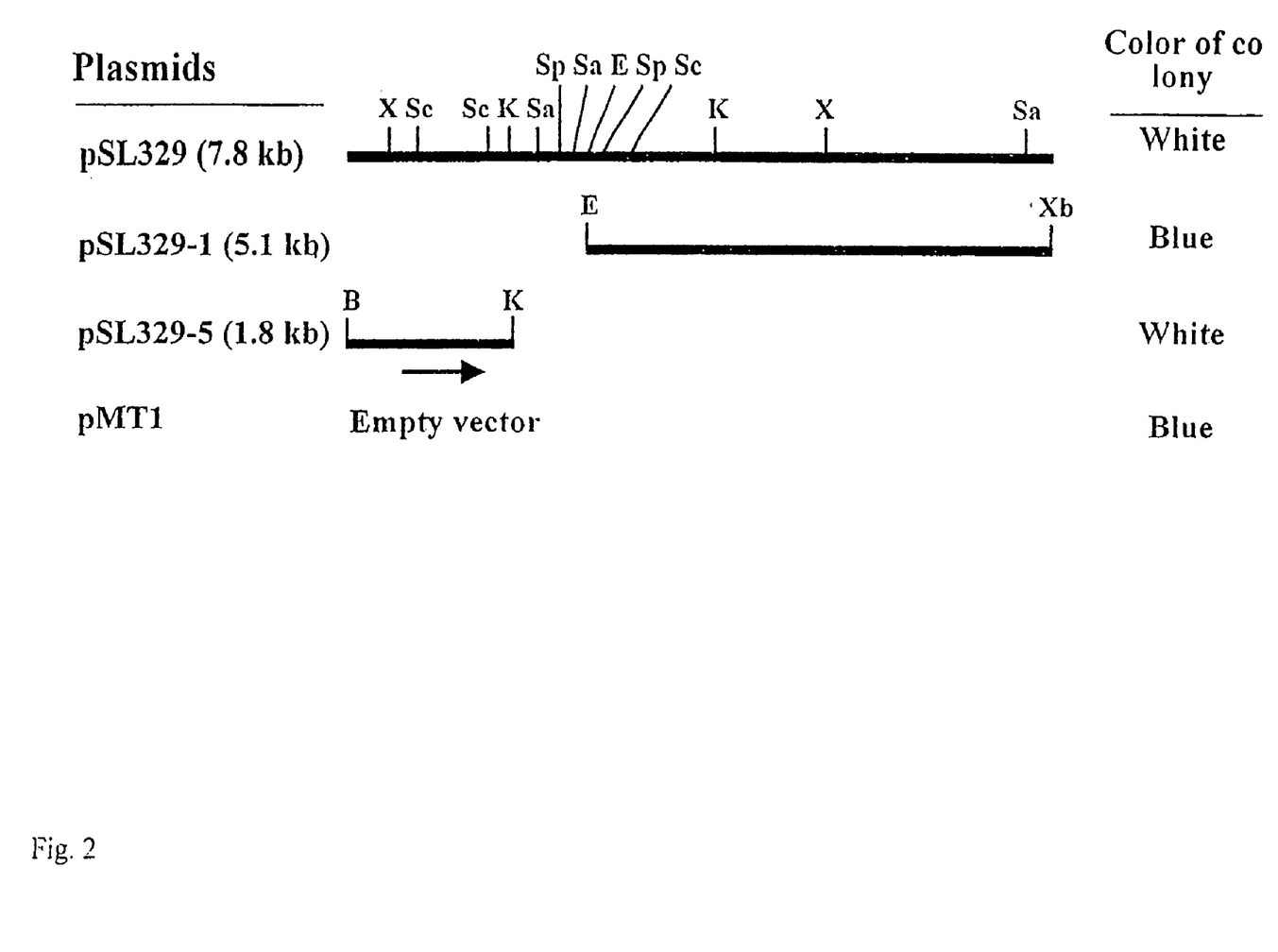

Isolation of glxR. To isolate genes whose protein products exert regulatory effect on the expression of the *C. glutamicum* aceB gene, we utilized pSL145 [Kim et al, 2001] carrying the enteric lac operon fused to the downstream of Corynebacterial aceB as the reporter plasmid. With the plasmid, modulation of aceB expression at the promoter region is reflected as changes in the β-galactosidase activity. *E. coli* DH5αF' cells carrying pSL145 (*E. coli* DH5αF'-145) formed blue colonies on LB plates containing X-gal and were used as the host for screening the Corynebacterial library. The host cell carrying a clone whose protein product has regulatory effect on the promoter region of aceB, thus affecting the expression of lacZ, was expected to form a white colony on the plate. Among a total of 20,000 colonies screened, 4 white colonies were identified. The cloned DNA turned out to contain overlapping inserts. Among the clones, plasmid pSL329 (FIG. 2), which carries a 7.8 kb insert, was chosen and analyzed further. The DNA region responsible for modulating the β-galactosidase activity was identified by patching cells carrying the subclones on LB media containing X-gal (FIG. 2). In accordance with the color test data, *E. coli* DH5αF'-145 cells carrying plasmid pSL329 showed 2.5 mU of β-galactosidase activity, a 90% reduction compared to the parental strain which showed 27 mU of β-galactosidase activity (Table 3). The data suggest that the gene (glxR, see below) carried in the cloned DNA expresses protein which may bind to the promoter region of the aceB gene to interfere with the expression of lacZ.

Figure 3:
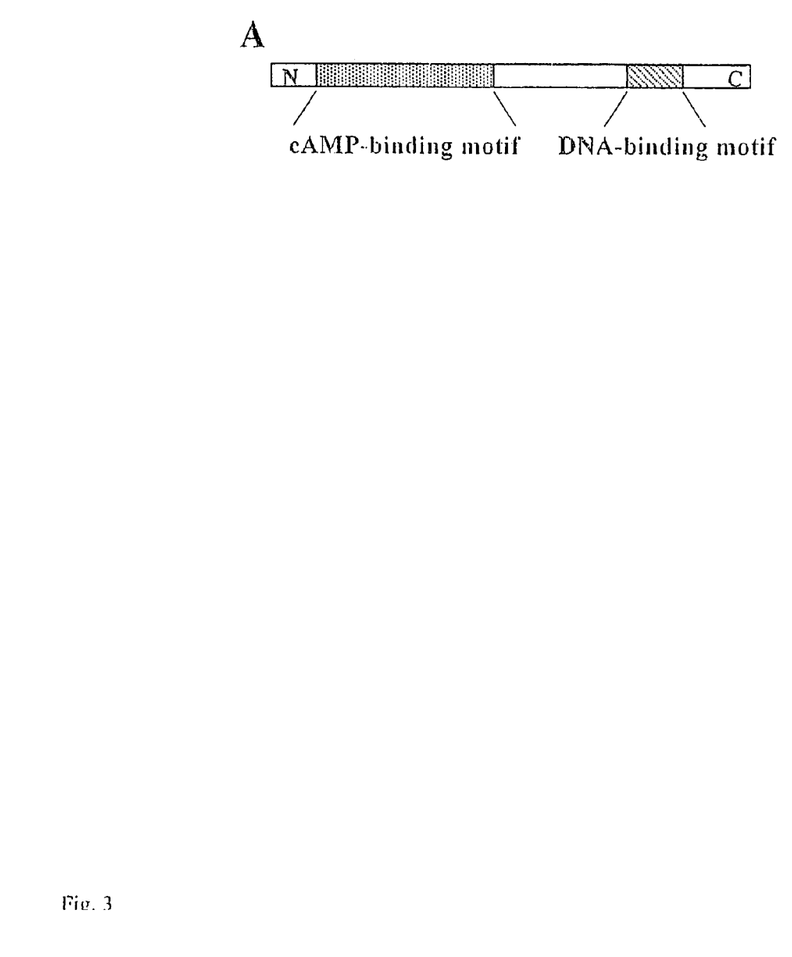
FIG. 3. Schematic diagram of the GlxR protein (Panel A).

Sequence analysis of the glxR gene. The complete nucleotide sequence of the clone was determined using pSL329-5 as the sequencing template. An ORF consisted of 684 bp was found in the central region of the clone. As based on the similarities with other proteins (see below), the GTG was chosen as the start codon (FIG. 3). A potential ribosome-binding site of AGGA was located 9 bp upstream from the GTG (FIG. 3). The GC content of the ORF was 59%, which is typical of *C. glutamicum* genes. The codon preference was also very similar to the previously reported Corynebacterial genes and, interestingly, it also indicated that the ORF could encode a protein that is expressed at a low level [Malumbres et al, 1993].

Figure 4:
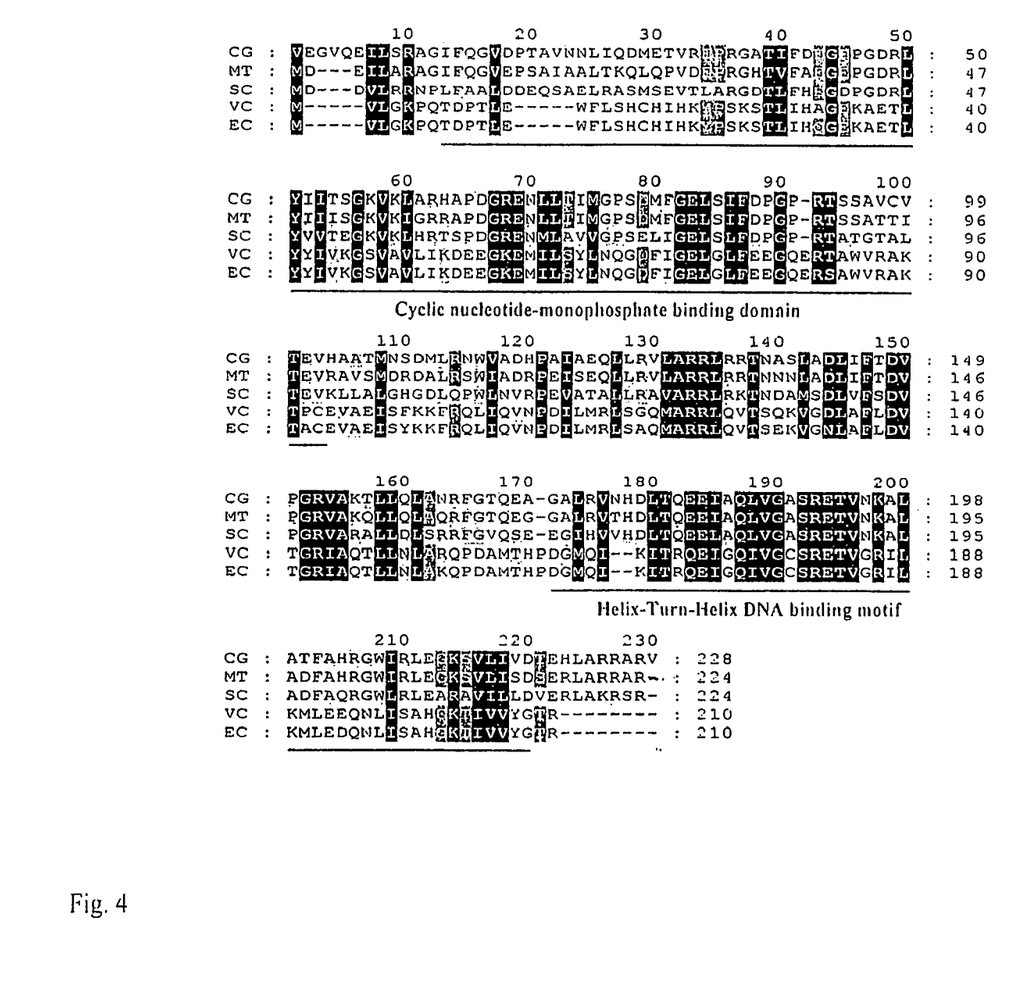

The putative gene product consisted of 228 amino acids (SEQ ID NO:1) encoding a 24,957 Da protein with the predicted isoelectric point of 7.0. The translated amino-acid sequence of the ORF was compared with the sequences in the protein database. Among the known proteins, a putative transcriptional regulatory protein of *Mycobacterium tuberculosis* (E70790) and a putative transcriptional regulatory protein of *Streptomyces coelicolor* (T36556) gave the highest-score with the amino acid identity of 78 and 53%, respectively. Among the proteins whose roles are known, the cyclic AMP receptor protein (CRP) of *Vibrio cholerae* (NP232242), *Salmonella typhimurium* (A26049), and *E. coli* (J01598) gave the highest score with approximately 27% identity. Close analysis of the amino acid sequences revealed 2 conserved motifs that may be involved in the catalytic activity of the enzyme (FIG. 3). Amino acids from 13 to 102 showed a pattern of conserved residues anticipated for a cAMP-binding domain, showing 31% identity with consensus sequences for cNMP-binding domains (FIG. 4). In addition, a helix-turn-helix DNA binding motif of CRP/FNR family was identified in the carboxy terminal region (from amino acid 170 to 218) of the encoded protein. It showed 41% identity with the helix-turn-helix motif of CRP (FIG. 4). Based on the characteristics of the cloned gene (see below), we named the Corynebacterial gene as glxR (glyoxylate bypass regulator).

Figure 5:
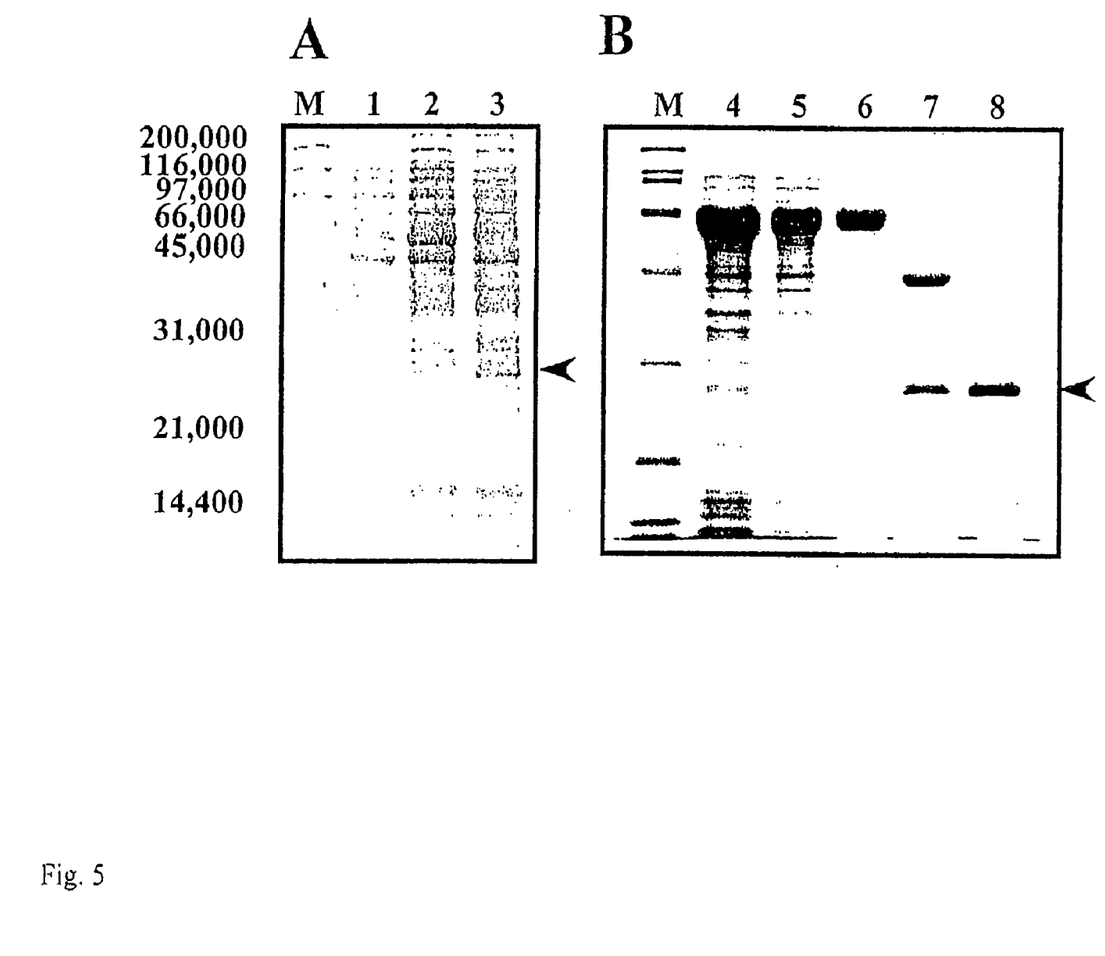

Analysis of the encoded protein. Cloning the glxR coding region including the RBS into the pKK223-3 vector and introducing the resulting vector into *E. coli* resulted in the expression of $M_r$ of 25,000 protein on SDS-PAGE (FIG. 5A). The observed molecular weight agreed with the predicted Mw of the protein. The GlxR protein was purified by utilizing the MBP fusion technique. As expected, the purified protein showed $M_r$ of 25,000 on SDS-PAGE (FIG. 5B).

The native Mw of the purified protein was 44,000 Da as determined by gel-filtration column chromatography (data not shown). This suggests that the proteins are likely to form dimers like most other DNA-binding proteins.

Figure 6:
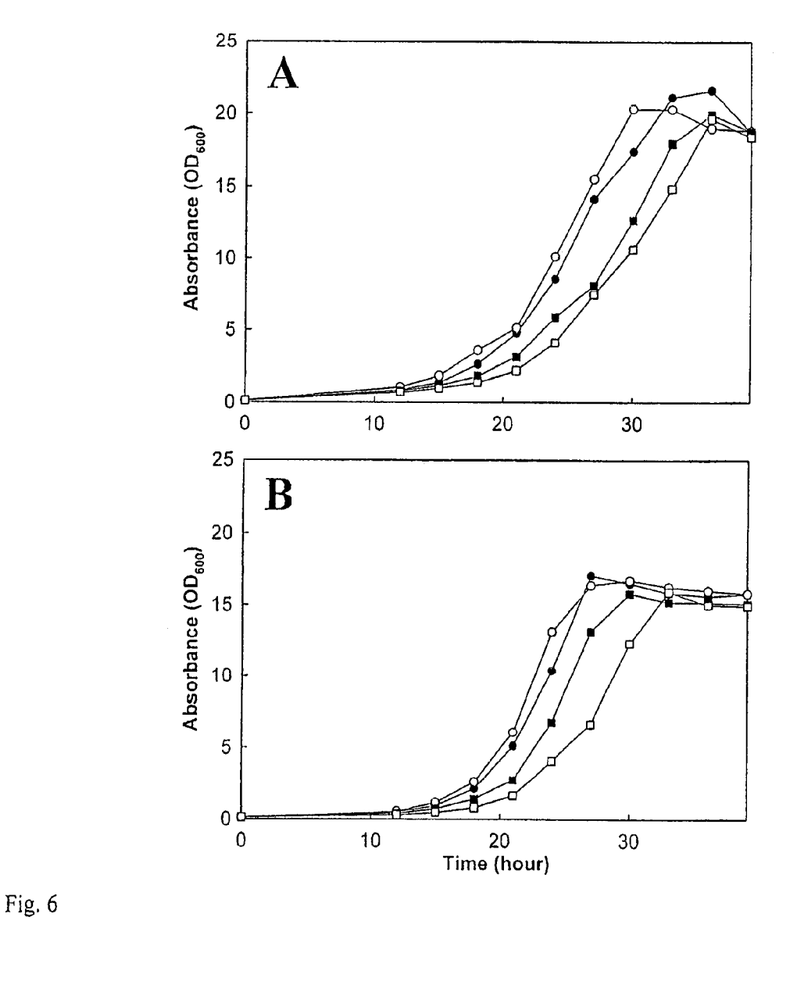
FIG. 6. Expression of glxR in *C. glutamicum* and the effect of cAMP on growth. Glucose (panel A) or acetate (panel B) was used as the sole carbon source. When necessary, cAMP was added to the final concentration of 8 mM. Symbols: ●, pMT1 (empty vector); ○, pMT1 and cAMP; ■, pSL329-5 (glxR); □, pSL329-5 (glxR) and cAMP.

Involvement of cAMP. As the first step to study the role of glxR, plasmid pSL329-5, a glxR clone, was introduced into *C. glutamicum* AS019E12 and the effect was monitored. As shown in FIG. 6AB, the presence of a glxR clone in multicopy significantly affected the growth of the host cell grown on glucose or acetate as the carbon source. As shown in Table 2, the growth impairment observed in acetate minimal medium was apparently due to the decrease of the glyoxylate bypass enzymes, such as malate synthease and isocitrate lyase. The enzymatic activity of isocitrate dehydrogenase, a TCA cycle enzyme, was unaffected. The reduction in the activity was due to the reduction in the amount of expressed enzymes as judged by SDS-PAGE (data not shown). However, when the growth experiment was carried out in the presence of cAMP, an interesting result was observed. Unlike the growth in glucose minimal medium (FIG. 6A), growth of cells carrying the glxR clone in acetate minimal medium was severely affected by cAMP (FIG. 6B). Under both growth conditions with glucose or acetate as the carbon source, the amount of expressed GlxR was unaffected as evidenced by Western blot analysis (data not shown). In agreement with the data, as shown in Table 3, the modulating activity of a glxR clone at the Corynebacterial aceB promoter was not observed in the cya mutant strain of *E. coli*. In addition, the purified GlxR protein was more resistant to digestion by trypsin in the presence of cAMP (data not shown). These data suggest that cAMP is involved in modulating the GlxR activity. It also suggests that cAMP might be a signaling molecule for controlling the expression of genes involved in the utilization of various carbon sources.

Figure 7:
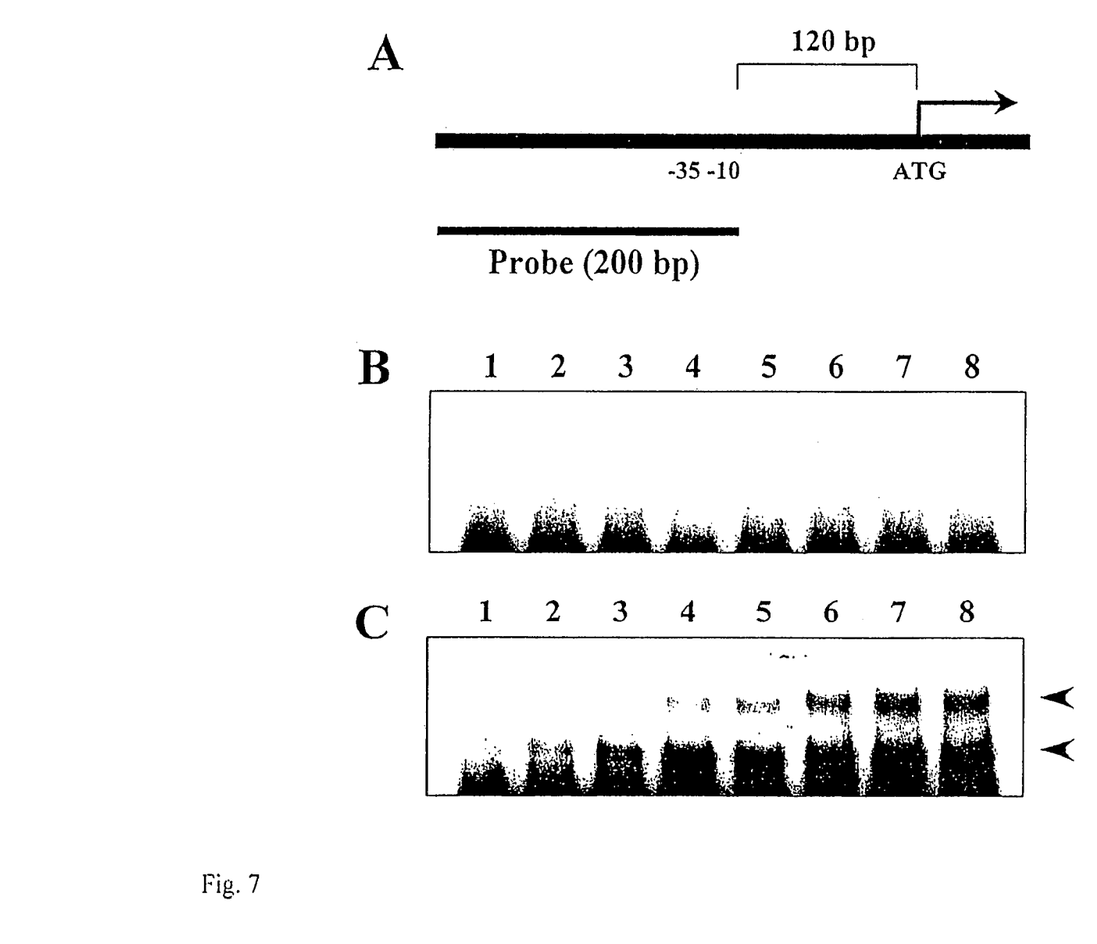

DNA-binding activity of GlxR. Knowing that GlxR is involved in controlling the expression of aceB, we tested binding of purified GlxR on the promoter region of the aceB gene. For the purpose a DNA fragment which carries the promoter region of the aceB gene was utilized (FIG. 7A). In the presence of cAMP, addition of increasing amounts of purified GlxR protein to the probe resulted in two differently shifted bands (FIG. 7C). The upper band appeared later than the lower band, suggesting that the upper bands might be due to the oligormerization of the GlxR proteins. Replacing cAMP with acetyl-CoA which has been suggested as a modulator for the glyoxylate bypass enzymes [Wendisch et al, 1997] did not result in any DNA shifts with the probe (data not shown). Knowing that GlxR protein may form oligomers as evidenced by gel mobility assay, we tested oligomerization of purified GlxR with EDAC, a crosslinking agent. Irrespective of the presence of cAMP, crosslinked structures of dimmers and tetramers were observed.

Muteins of the glxR proteins. Starting from the original glxR polypeptide sequence (SEQ ID NO:1) a lot of functional equivalent glxR muteins can be prepared by substituting, by inserting or by deleting one or more of the amino acids of SEQ ID NO:1. Functional equivalent muteins means that these muteins have still the ability to bind to cAMP and to repress the expression, specifically the transcription of the aceB gene of *C. glutamicum* in an order of magnitude which is the same as with glxR having the SEQ ID NO:1. The preparation of glxR muteins is preferably done by well known genetic engineering techniques such as site directed mutagenesis of the respective encoding polynucleotide sequences.

The glxR muteins differ from the SEQ ID NO:1 sequence in up to 20%, preferred up to 15%, most preferred up to 10% and very most preferred up to 5% of the amino acid sequence.

It is important, that the glxR muteins possess an intact cAMP binding domain and an intact helix-turn-helix DNA binding motif as defined for example in FIG. 4.

Materials and Methods

Bacterial strains, plasmids, and growth conditions. All strains and plasmids used in this study are listed in Table 1. *E. coli* DH5αF' was used for the construction and propagation of plasmids. *E. coli* JM105 was used to express GlxR from pKK-glxR. Operon fusion of $P_{aceB}$-lacz constructed on plasmid pRS415 was transferred to the chromosome of *E. coli* strains using λRS415 lambda phage as described by Simons et al. [Simons et al, 1987]. Otherwise stated, *E. coli* and *C. glutamicum* cells were cultured at 37° C. in LB [Sambrook et al, 1989] and at 30° C. in MB [Follettie et al, 1993], respectively. Minimal media for *E. coli* and *C. glutamicum* were M9 [Sambrook et al, 1989] and MCGC [von der Osten, 1989], respectively. Carbon sources were added to the minimal medium in following amounts: glucose, 1%; acetate, 2%. Antibiotics were added in following amounts: ampicillin, 50 µg/ml; tetracycline, 20 µg/ml; kanamycin, 20 µg/ml. X-gal and cAMP were added to medium at 40 µg/ml and 8 mM, respectively. For the expression of proteins, IPTG was added to the final concentration of 1 mM or 0.3 mM.

DNA technology. Standard molecular cloning, transformation, and electrophoresis procedures were used [Sambrook et ali 1989]. Plasmids were introduced into *C. glutamicum* cells by electroporation [Follettie et al, 1993]. Mini plasmid preparation for *C. glutamicum* cells was performed as described [Yoshihama et al, 1985]. Chromosomal DNA from *C. glutamicum* AS019 was prepared as described [Tomioka et al, 1981]. Restriction enzymes and DNA modifying enzymes were purchased from Takara Shuzo Co. (Shiga, Japan) and New England Biolabs (Beverly, USA) and used as recommended by the manufacturer.

Cloning and sequencing. The genomic library of *C. glutamicum* AS019 was constructed as previously described [Lee and Sinskey, 1994]. It was made of 4 to 13 kb MboI fragments cloned into the *E. coli-Corynebacterium* shuttle vector pMT1. *E. coli* DH5αF' cells were transformed with pSL145 [Kim et al, 2001], and the resulting *E. coli* DH5αF'-145 strain was used as the host for screening the library. Plasmid pSL 145 carries lacZYA fused to the downstream of the aceB promoter region.

For nucleotide sequence analysis of glxR, plasmids pSL329-5 was used as the template. The complete nucleotide sequence of glxR was determined commercially at the Korea Research Center for Basic Sciences (Taejon, Korea) using universal and synthetic oligonucleotide primers. A sequence similarity search of nucleotide and amino acid sequences was performed at the National Center for Biotechnology Information (http://www.ncbi.nlm.nih.gov/BLAST/) using BLAST [Altschul et al, 1990; Altschul et al, 1997]. Pairwise sequence alignments were performed at the website of ExPASy Proteomics Tools (http://www.expasy.ch/tools/) using the ClustalW alignment method [Thompson et al, 1994].

Construction of plasmids. Plasmids pSL329-1, pSL329-2, pSL329-3 and pSL329-5 were made by ligating the 5.1 kb EcoRI-XbaI fragment, 5.2 kb XhoI fragment, 2.7 kb SmaI-EcoRI fragment, and 1.8 kb KpnI fragment of pSL329 into the pMT1 vector digested with SmaI-XbaI, XhoI, and KpnI, respectively. Plasmid pSL329-4 was made by deleting the 0.2 kb SalI fragment of pSL329-3. Plasmid pSL08-glxR was constructed by inserting the 1.8 kb KpnI-BamHI frgment of pSL329-5 into pSL08 which was digested with XbaI and blunt-ended with Klenow enzymes. The direction of transcription of the cloned glxR gene was opposite to that of the aceB gene. Plasmid pKK-glxR was constructed by amplifying the 828 bp fragment of pSL329-5 with C1 and C2 primers and inserting the resulting fragment into the EcoRI site of pKK223-3. The 828 bp fragment carries the glxR gene and its ribosome-binding site. Plasmid pMAL-glxR was constructed as follows. The glxR coding region was amplified with primers of D1 and D2 using plasmid pSL329-5 as a template. The 0.89 kb PCR product was treated with EcoRI and SalI, and ligated into the EcoRI-SalI digested and dephosphorylated pMAL-c2.

Purification of GlxR. Plasmid pMAL-glxR was used to express GlxR. The vector carries glxR fused to malE and expresses MBP-GlxR fusion protein. The cleavage of the fusion protein with Factor Xa releases a free GlxR protein with a string of amino acids (Ile-Ser-Val-Phe) attatched to the N-terminus of the protein. The fusion protein was expressed and purified as suggested by the manufacturer of the vector pMAL-c2 (New England Biolabs, Beverly, USA). GlxR was separated from MBP by Q-Sepharose Fast Flow column chromatography (Amersham Pharmacia Biotech, 2.8 cm by 11 cm) using a linear NaCl gradient of 25–500 mM. Fractions containing the GlxR were pooled and the protein was concentrated by dialysis against PEG 8,000.

Gel mobility shift assay. The probe DNA was prepared as follows. The 200 bp DNA fragment which includes an upstream region of the aceB gene (from 120 to 320 bp upstream from the ATG start codon) was amplified using E1 and E2 primers and subsequently labeled with [$\gamma$-$^{32}$P]dATP using T4 polynucleotide kinase. A binding reaction mixture of 10 µl contained the labeled DNA fragments, various amount of purified GlxR, 10 mM phosphate buffer, 137 mM NaCl, 2.7 mM KCl, 3 µg of bovine serum albumin, and 1 µg of poly[dI-dC] poly[dI-dC]. The binding of GlxR to the probe DNA was performed at room temperature for 15 min and the mixture was analyzed in 6% native polyacrylamide gels as described [Sambrook et al, 1989]. When necessary, 0.2 mM cAMP was included in the binding buffer, gels, and the running buffer.

Biochemical analysis and preparation of antibody. Corynebacterial cell extracts were prepared as described [Follettie et al, 1993]. The enzymatic activities of β-galactosidase, malate synthase, isocitrate lyase, isocitrate dehydrogenase, and acetate kinase were determined as previously described. [Miller, 1972; Gubler et al, 1993; Dixon and Kornberg, 1959; Garnak and Reeves, 1979; van Dyk and LaRossa, 1987] Protein was measured by the method of Bradford, with bovine serum albumin as the standard [Bradford, 1976]. SDS-PAGE and Western blot analysis were performed as previously described [Laemmli, 1970]. The anti-GlxR antiserum was prepared commercially at Koma Biotech (Seoul, Korea) using a mouse as the host.

GenBank accession number. The nucleotide sequence of glxR was deposited in GenBank under the accession number of AF293334.

Discussion

In this study, we showed involvement of GlxR in the regulation of the aceB gene which is involved in the utilization of acetate as a carbon source. The evidences were, 1) modulation of the β-galactosedase activity in the reporter-carrying *E. coli*, 2) presence of a putative DNA-binding domain in the encoded protein sequence, 3) decresed expression of glyoxylate bypass enzymes in the presence of introduced glxR clone, and 4) DNA binding of the purified GlxR on the aceB promoter region. In addition, like other DNA-binding proteins, the finding that the protein present as dimers with relatively basic pI also support regulatory role for the protein. Although our data suggest that the glxR gene might be primarily involved in the regulation of glyoxylate bypass genes, such as aceA and aceB, we can not rule out the possibility that the gene may also be involved in the expression of other genes. The growth retardation by glxR in glucose minimal medium may suggest interaction of the GlxR protein with other promoters, although this could be due to the sequence-independent affinity for DNA as observed with CRP. Despite numerous attempts, failure to construct a glxR mutant strain using the cloned DNA may suggest essentiality of the gene (data not shown), suggesting the involvement of the glxR gene for the expression of other genes. In this respect, like CRP of *E. coli*, the GlxR protein could function as an activator for other genes, making the gene essential.

It is interesting to know that the encoded protein sequence of the glxR gene shows homology with CRP of enteric bacteria. CRP plays a role in carbon catabolite repression, which is governed by cAMP in enteric bacteria, such as *E. coli*. The major similarities between GlxR and CRP include, 1) amino acid sequence similarity, 2) the presence of cAMP-binding-motif, 3) the involvement of cAMP for modulation of the DNA-binding activity, and 4) differential sensitivity of the protein to protease in the presence of cAMP. Despite these similarities, however, the role of GlxR appears to be distinct form that of CRP. For instance, the glxR gene could not complement the crp mutant of *E. coli* (data not shown).

Cyclic AMP is an important signaling molecule controlling the expression of many genes. Involvement of cAMP has been reported in many bacteria, such as enteric bacteria, *Bacillus* species, and *Streptomyces* species [Botsford and Harman, 1992]. In *E. coli*, the molecule plays important roles for carbon catabolite genes, such as lactose and arabinose operons [Epstein et al, 1975]. Under conditions of carbon starvation, the intracellular concentration of cAMP is elevated. Although this is a general phenomenon, there are also exceptions. For example, *Brevibacterium* species apparently keep the concentration of cAMP low when grown on glucose minimal media [Peter et al, 1991]. This is similar to what we found with *C. glutamicum*. As evidenced in the growth experiment (FIG. 6), the intracellular concentration of cAMP may be kept low when grown on acetate. Decreased growth of cells carrying the glxR clone in the presence of cAMP may support this hypothesis. This is further supported by the data obtained in the glucose minimal medium which showed no apparent effect with cAMP. Although, this is in contrast to the dogma established in *E. coli*, in *Streptomyces* species, it has been claimed that cAMP is present at highest levels during periods of rapid growth rather than glucose limited conditions and thus signals the availability rather than the lack of carbon sources [Dobrova et al., 1984]. Although cAMP-independent mechanism of catabolite repression in low GC content Gm+bacteria, such as *Bacillus* sp. has been studied in detail, the information in high GC content Gm+ bacteria, such as Corynebacterium species, is wholly lacking (for reviews see Botsford and Harman, 1992; Saier Jr., 1996). In this respect, this study shows the first evidence for the involvement of cAMP in the expression of genes involved in carbon utilization. In conclusion, we successfully isolated a regulatory gene from *C. glutamicum* using a reporter plasmid carrying the Corynebacterial aceB promoter and enteric lac operon. Although the glxR gene appear to encode repressor-like proteins for the aceA and aceB genes, there is a possibility that the gene might be also involved in the expression of other genes.

REFERANCES

Altschul, S. F., W. Gish, W. Miller, E. W. Myers, and D. J. Lipman. 1990. Basic local alignment search tool. *J. Mol. Biol.* 215:403–410.

Altschul, S. F., T. L. Madden, A. A. Schäffer, J. Zhang, Z. Zhang, W. Miller, and D. J. Lipman. 1997. Gapped BLAST and PSI-BLAST: a new generation of protein database search programs. *Nucleic Acids Res.* 25:3389–3402.

Botsford, J. L. and J. G. Harman. 1992. Cyclic AMP in prokaryotes. *Microbiol. Rev.* 56:100–122.

Bradford, M. M. 1976. A rapid and sensitive method for the quantification of microgram quantities of protein utilizing the principle of protein-dye binding. *Anal. Biochem.* 72:248–254.

Chung, T., D. J. Klumpp, and D. C. LaPorte. 1988. Glyoxylate bypass operon of *Escherichia coli*: cloning and determination of the functional map. *J. Bacteriol.* 170:386–392.

Cossart, P., and B. Gicquel-Sansey. 1985. Regulation of expression of the crp gene of *E. coli* K12: In vivo study. *J. Bacteriol.* 161:454–457.

Dixon, G. H. and H. L. Kornberg. 1959. Assay methods for key enzymes of the glyoxylate cycle. *Biochem. J.* 72:3P.

van Dyk, T. K. and R. A. LaRossa. 1987. Imvolvement of ack-pta operon products in a-ketobutyrate metabolism by *Salmonella typhimurium*. *Mol. Gen. Genet.* 207:435–440.

Dobravá, Z., Naprstek, J., Jiresová, M. and J. Janecek. 1984. cAMP and adenylate cyclase in *Streptomyces granaticolor*. *FEMS Microbiol. Lett.* 11:197–200.

Epstein, W., L. B. Rothman-Denes, and J. Hesse. 1975. Adenosine 3':5'-cyclic monophosphate as mediator of catabolite repression in *Escherichia coli*. *Proc. Nat. Acad. Sci. USA* 6:2300–2304.

Follettie, M. T., O. Peoples, C. Agoropoulou, and A. J. Sinskey. 1993. Gene structure and expression of the *Corynebacterium flavum* N13 ask-asd operon. *J. Bacteriol.* 175:4096–4103.

Garnak, M. and H. Reeves. 1979. Purification and properties of phosphorylated isocitrate dehydrogenase of *Escherichia coli*. *J. Biol. Chem.* 254:7915–7920.

Gubler, M., S. M. Park, M. Jetten, G. Stephanopoulos, and A. J. Sinskey. 1993. Effects of phosphoenol pyruvate carboxylase deficiency on metabolism and lysine production in *Corynebacterium glutamicum*. *Appl. Microbiol. Biotechnol.* 40:857–863

Jetten, M. S. M., M. E., Gubler, S. H. Lee, and A. J. Sinskey. 1994. Structural and functional analysis of pyruvate kinase from *Corynebacterium glutamicum*. *Appl. Envi-ron. Microbiol.* 60:2501–2507

Kim, H.-J., Y. Kim, M.-S. Lee, and H.-S. Lee. 2001. Gene lmrB of *Corynebacterium glutamicum* confers efflux-mediated resistance to lincomycin. *Mol. Cells* 12:112–116.

Kinoshita, S. 1995. Glutamic acid bacteria, p. 115–142. In A. L. Demain, and N. A. Solomon (ed.), *Biology of industrial microorganisms*. Benzamin/Cummings Publishing Company, London.

Laemmli, U. K. 1970. Cleavage of structural proteins during the assembly of the head of bacteriophage T4. *Nature (London)* 227:680–685.

Lee, H.-S., and A. J. Sinskey. 1994. Molecular characterization of aceB, a gene encoding malate synthase in *Corynebacterium glutamicum*. *J. Microbiol. Biotechnol.* 4:256–263.

Malumbres, M., J. A. Gil, and J. F. Martin. 1993. Codon preference in corynebacteria. *Gene* 134:15–24.

Malumbres, M. and J. F. Martin. 1996. Molecular control mechanisms of lysine and Threonine biosynthesis in amino acid-producing corynebacteria: Redirecting carbon flow. *FEMS Microbiol. Lett.* 143:103–114.

Miller, J. H. 1972. Experiments in molecular genetics. Cold Spring Harbor Laboratory Press, Cold Spring Harbor, N.Y.

von der Osten, C. Gioannettie, and A. J. Sinskey. 1989. Design of a defined medium for growth of *Corynebacterium glutamicum* in which citrate facilitate iron uptake. *Biotechnology Letters* 11:11–16.

Peters, E. P., A. F. Wilderspin, S. P. Wood, M. J., J. M. Zvelebil, O. Sezer, and A. Danchin. 1991. A pyruvate-stimulated adenylate cyclase has a sequence related to the fes/fps oncogenes and to eukaryotic cyclases. *Mol. Microbiol.* 5:1175–1181.

Reinscheid, D. J., B. J. Eikmanns, and H. Sahm. 1994. Characterization of the isocitrate lyase gene from *Corynebacterium glutamicum* and biochemical analysis of the enzyme. *J. Bacteriol.* 176:3474–3483.

Reinscheid, D. J., B. J. Eikmanns, and H. Sahm. 1994. Malate synthase from *Corynebacterium glutamicum*: sequence analysis of the gene and biochemical characterization of the enzyme. *Microbiology* 140:3099–3108.

Sahm, H., L. Eggeling, B. Eikmanns, and R. Kramer. 1995. Metabolic design in amino acid producing bacterium *Corynebacterium glutamicum*. *FEMS Microbiol. Rev.* 16:243–252.

Saier Jr., M. H. 1996. Cyclic AMP-independent catabolic repression in bacteria. *FEMS Microbiol. Lett.* 138:97–103.

Sambrook, J., E. F. Fritsch, and T. Maniatis. 1989. Molecular cloning: a laboratory manual, 2nd ed. Cold Spring Harbor Laboratory, Cold Spring Harbor, N.Y.

Sanger, F., A. R. Coulson, G. F. Hong, D. F. Hill, and G. B. Peterson. 1982. Nucleotide sequence of bacteriophage λDNA. *J. Mol. Biol.* 162:729–773.

Simons, R. W., F. Houman, and N. Kleckner. 1987. Improved single and multicopy lac-based cloning vectors for protein and operon fusions. *Gene* 53:85–96.

Sunnarborg, A., D. Klumpp, T. Chung, and D. C. LaPorte. 1990. Regulation of the glyoxylate bypass operon: cloning and characterization of iclR. *J. Bacteriol.* 172:2642–2649.

Tomioka, N., K. Shinozaki, and M. Sugiura. 1981. Molecular cloning and characterization of ribosomal RNA genes from a blue-green alga, *Anacystis nidulans*. *Mol. Gen. Genet.* 184:359–363.

Thompson, J. D., D. G. Higgins, and T. J. Gibson. 1994. CLUSTAL W: improving the sensitivity of progressive multiple sequence alignment through sequence weighting, position-specific gap penalties and weight matrix choice. *Nucleic Acids Res.* 22:4673–4680.

Wendisch, V. F., M. Spies, D. J. Reinschied, S. Schnicke, H. Sahm, and B. J. Eikmanns. 1997. Regulation of acetate metabolism in *Corynebacterium glutamicum*: transcriptional control of the isocitrate lyase and malate synthase genes. *Arch. Microbiol.* 168:262–269.

Yoshihama, M., K. Higashiro, E. A. Rao, M. Akedo, W. G. Shanabruch, M. T. Follettie, G. C. Walker, and A. J. Sinskey. 1995. Cloning vector system for *Corynebacterium glutamicum*. *J. Bacteriol.* 162:591–597.

FIGURE LEGENDS

FIG. 1. The glyoxylate bypass and associated pathways of *Corynebacterium glutamicum*. The glyoxylate bypass is carried out by isocitrate lyase and malate synthase. Abbreviations: ACK, acetate kinase; ICDH, isocitrate dehydrogenase; ICL, isocitrate lyase; MS, malate synthase; OAA, oxaloacetate; PTA, phosphotransacetylase. Dashed arrows indicate multiple steps.

FIG. 2. Schematic diagram of clones and subclones. Plasmids pSL329 was isolated from the Corynebacterial genomic library. The cloning vector pMT1 is not shown. The colony color (blue or white) of the *E. coli* DH5αF'-145 cells carrying each clone was tested on LB plates containing X-gal, tetracycline, and ampicillin. Abbreviations: B, BamHI; E, EcoRI; K, KpnI; Sa, SalI; Sc, ScaI; Sp, SphI; X, XhoI; Xb, XbaI.

FIG. 4. Multiple sequence alignment of the GlxR protein of *C. glutamicum* with other homologous sequences. Conserved and functionally similar amino acids are marked with black and shaded boxes, respectively. Cyclic nucleotide-monophosphate binding motif and helix-turn-helix DNA binding motif are marked with solid bars. Abbreviations: CG, GlxR of *C. glutamicum* (AF220150); MT, putative transcriptional regulator Rv3676 of *Mycobacterium tuberculosis* H37RV (E70790); SC, putative transcriptional regulator of *Streptomyces coelicolor* (T36556); VC, CRP of *Vibrio cholerae* (NP232242); EC, CRP of *Escherichia coli* (J01598).

FIG. 5. Expression of GlxR in *E. coli*. (A) The GlxR protein was expressed from the pKK-glxR vector as described in the Materials and Methods. Lanes: 1, *E. coli* JM105/pKK223-3; 2, *E. coli* JM105/pKK-glxR (uninduced); 3, *E. coli* JM105/pKK-glxR (induced). (B) Purification of GlxR. The protein was expressed from pMAL-glxR. Lanes: 4, total protein; 5, soluble fraction; 6, purified MBP-GlxR fusion protein; 7, after Factor X treatment; 8, purified GlxR protein. M indicates molecular weight standard.

FIG. 7. Gel shift assay using purified GlxR. Purified GlxR proteins were incubated with probe and the mixtures were analyzed by 6% PAGE. Panels: A, schematic diagram of the aceB promoter region; B, gel shift in the absence of cAMP; C, gel shift in the presence of cAMP. Cyclic AMP was added (to 0.2 mM) to the assay mixture, gels, and the PAGE buffer. Lanes: 1, no protein; 2, 0.03 µg; 3, 0.06 µg; 4, 0.13 µg; 5, 0.25 µg; 6, 0.5 µg; 7, 1.0 µg; 8, 2.0 µg of purified GlxR protein. Arrows indicate shifted bands.

TABLE 1

Bacterial strains and plasmids used in this study

| Strains or plasmids | Relevant genotypes or phenotypesa | Sources or references |
| --- | --- | --- |
| *Escherichia coli* | | |
| E. coli DH5αF' | F⁻?80dlacZ?M15, recA1, endA1, gyrA96, thi-1, hsdR17(rk−, mk+), supE44, relA1, deoR, ?(lacZYA-argF)U169, ?⁻ | Bethesda Research Laboratories |
| E. coli JM105 | endA1, supE, sbcB15, thi, rpsL, ?(lac-proAB)/F'[traD36, proAB+, lacIq, lacZ?M15] | NIGa |
| E. coli P90C | ara, ?(lac-pro), thi | Simons et al., 1987 |
| E. coli TP2010 | xyl, cya, argH, lacX74, recA, ilvA, Srl::Tn10 | Cossart and Gicquel-Sansey, 1985 |
| E. coli DH5αF'-145 | E. coli DH5αF' containing plasmid pSL145. Screening host | Kim et al., 2001 |
| E. coli HL994 | E. coli DH5αF' containing chromosomal $P_{aceB}$-lacZYA fusion | This study |
| E. coli HL989 | E. coli TP2010 containing chromosomal $P_{aceB}$-lacZYA fusion | Kim et al., 2001 |
| *Corynebacterium glutamicum* | | |
| ASO19 | Spontaneous rifampin-resistant mutant of C. glutamicum ATCC13059b | Yoshihama et al., 1985 |
| ASO19E12 | Restriction-deficient variant of ASO19 | Follettie et al., 1993 |
| Plasmids | | |
| pBluescript SK(+) | Cloning vector, Apr, lacZ, 2,958 bp | Stratagene |
| pKK223-3 | Expression vector; $P_{tac}$, Apr, 4,587 bp | Amersham Pharmacia Biotech |
| pMAL-c2 | Expression vector, Apr, $P_{tac}$, malE, lacIq, lacZa, 6,723 bp | New England BioLabs |
| pRS415 | Promoter less lac operon fusion vector; Apr, 10,752 bp | Simons et al., 1987 |
| λRS45 | Phage vector for transferring fusions to single copy | Simons et al., 1987 |
| pMT1 | Shuttle vector; Apr, Kmr | Follettie et al., 1993 |
| pSL130 | pRS415 carrying 2.3 kb fragment including aceB promoter region, Apr | Kim et al., 2001 |
| pSL145 | $P_{aceB}$-lacZYA, Tcr | Kim et al., 2001 |
| pSL329 | pMT1 carrying 7.8 kb fragment including glxR | This study |
| pSL329-1 | pMT1 carrying 5.1 kb EcoRI-XbaI fragment of pSL329 | This study |
| pSL329-2 | pMT1 carrying 5.2 kb XhoI fragment of pSL329 | This study |
| pSL329-3 | pMT1 carrying 2.7 kb SmaI-EcoRI fragment of pSL329 | This study |
| pSL329-4 | pMT1 carrying 2.5 kb SmaI-SalI fragment of pSL329 | This study |
| pSL329-5 | pMT1 carrying 1.8 kb KpnI fragment of pSL329 | This study |
| pSL08 | pMT1 carrying 4.3 kb fragment including aceB | Lee et al., 1994 |
| pSL08-glxR | pSL08 carrying 1.8 kb KpnI-BamHI fragment including glxR of pSL329-5 | This study |
| pKK-glxR | pKK223-3 carrying 0.83 kb fragment including glxR | This study |
| pMAL-glxR | pMAL-c2 carrying 0.89 kb fragment including glxR | This study |
| Primersb | | |
| C1c | 5'CG<u>GAATTC</u>GATGTGTGCAGATGAAGG3' (SEQ ID NO: 2) | |
| C2 | 5'CG<u>GAATTC</u>TATTCGTTACCTGCAGGC3' (SEQ ID NO: 3) | |

TABLE 1-continued

Bacterial strains and plasmids used in this study

| Strains or plasmids | Relevant genotypes or phenotypes[a] | Sources or references |
|---|---|---|
| D1 | 5'CG<u>GAATTC</u>GTGGAAGGTGTACAGG3' (SEQ ID NO: 4) | |
| D2 | 5'ACGC<u>GTCGAC</u>TATTCGTTACCTGCAGG3' (SEQ ID NO: 5) | |
| E1 | 5'GGAAAATGCAGGCACCGC3' (SEQ ID NO: 6) | |
| E2 | 5'GACTACCTCTGGAATCTAGG3' (SEQ ID NO: 7) | |

[a]National Institute of Genetics, Japan
[b]Underlined sequences indicate either EcoRI or SalI sites.
[r]superscripts indicate resistance.
Ap, ampicillin;
Km, kanamycin;
Tc, tetracycline

TABLE 2

Activities of isocitrate lyase (ICL), malate synthase (MS), acetate kinase (ACK), and isocitrate dehydrogenase (ICDH)[a]

| Media | C source | Plasmids | Description | Specific activity[b], nmol min$^{-1}$ mg$^{-1}$ | | | |
|---|---|---|---|---|---|---|---|
| | | | | ICL | MS | ACK | ICDH |
| MM | Glucose | pMT1 | Empty vector | 9 | 40 | 267 | 12 |
| | | pSL329-5 | glxR | 10 | 32 | 155 | 21 |
| | Acetate | pMT1 | Empty vector | 971 | 460 | 478 | 26 |
| | | pSL329-5 | glxR | 68 | 38 | 337 | 22 |
| MB | Glucose | pMT1 | Empty vector | 43 | 22 | 249 | 433 |
| | | pSL329-5 | glxR | 34 | 18 | 159 | 562 |
| | Acetate | pMT1 | Empty vector | 528 | 567 | 198 | 1480 |
| | | pSL329-5 | glxR | 21 | 62 | 133 | 960 |

[a]The enzymes were induced by growing the *C. glutamicum* AS019E12 cells to the stationary phase on MB [Follettie et al, 1993] containing 2% sodium acetate.
[b]The activities of malate synthase, isocitrate lyase, and isocitrate dehydrogenase were measured as described [Gubler et al, 1993; Dixon and Kornberg, 1959; Garnak and Reeves, 1979]. Cell extracts were prepared as described [Follettie et al, 1993].
[c]Plasmids were introduced into *Corynebacterium* by electroporation [Follettie et al, 1993].

TABLE 3

Expression of GlxR in *E. coli* cya mutant

| Strains | Properties | Plasmids | β-galactosidase activity |
|---|---|---|---|
| *E. coli* DH5αF'-145 | — | pMT1 | 27 |
| | — | pSL329-5 | 2.5 |
| *E. coli* HL994 | — | pMT1 | 237 |
| | — | pSL329-5 | 128 |
| *E. coli* HL989 | cya mutant | pMT1 | 5940 |
| | cya mutant | pSL329-5 | 5150 |

The invention claimed is:

1. An isolated polynucleotide molecule encoding a polypeptide comprising the amino acid sequence of SEQ ID NO: 1, or the complement thereof.

2. A method of modulating the expression of aceB in *Corynebacteria glutamicum* comprising introducing the polynucleotide molecule of claim 1 in *Corynebacteria glutamicum*.

3. The method of claim 2, wherein the method influences the biosynthesis of amino acids.

4. The method of claim 2, wherein the method increases the biosynthesis of amino acids.

5. The method of claim 4, wherein the amino acid is lysine.

6. A method of producing lysine in a host cell of the genus *Corynebacterium glutamicum* by influencing the gene expression of at least the aceB gene by modulating the expression of the polynucleotide molecule of claim 1 in said host cell.

7. The isolated polynucleotide molecule of claim 1, wherein the polypeptide binds cAMP.

8. The isolated polynucleotide molecule of claim 1, wherein the polypeptide represses the expression of the aceB gene of *Corynebacteria glutamicum*.

9. A vector comprising the polynucleotide molecule of claim 1.

10. The vector of claim 9, which is an expression vector.

11. An isolated host cell transfected with the expression vector of claim 10.

12. The host cell of claim 10, wherein said cell belongs to the genus *Corynebacterium*.

13. The method of claim 2, wherein the polynucleotide molecule is introduced by recombinant methods.

* * * * *

UNITED STATES PATENT AND TRADEMARK OFFICE
CERTIFICATE OF CORRECTION

| | |
|---|---|
| PATENT NO. | : 7,192,749 B2 |
| APPLICATION NO. | : 10/514076 |
| DATED | : March 20, 2007 |
| INVENTOR(S) | : Corinna Klopprogge et al. |

It is certified that error appears in the above-identified patent and that said Letters Patent is hereby corrected as shown below:

In the Claims:

In Claim 12, at Column 18, Line 48, replace "claim 10" with "claim 11" so it should correctly appear as: --claim 11--.

Signed and Sealed this

Eleventh Day of September, 2007

JON W. DUDAS
*Director of the United States Patent and Trademark Office*

SEQUENCE LISTING

<160> NUMBER OF SEQ ID NOS: 7

<210> SEQ ID NO 1
<211> LENGTH: 228
<212> TYPE: PRT
<213> ORGANISM: Corynebacterium glutamicum

<400> SEQUENCE: 1

Val Glu Gly Val Gln Glu Ile Leu Ser Arg Ala Gly Ile Phe Gln Gly
 1               5                  10                  15

Val Asp Pro Thr Ala Val Asn Asn Leu Ile Gln Asp Met Glu Thr Val
            20                  25                  30

```
Arg Phe Pro Arg Gly Ala Thr Ile Phe Asp Glu Gly Glu Pro Gly Asp
            35                  40                  45

Arg Leu Tyr Ile Ile Thr Ser Gly Lys Val Lys Leu Ala Arg His Ala
 50                  55                  60

Pro Asp Gly Arg Glu Asn Leu Leu Thr Ile Met Gly Pro Ser Asp Met
 65                  70                  75                  80

Phe Gly Glu Leu Ser Ile Phe Asp Pro Gly Pro Arg Thr Ser Ser Ala
                 85                  90                  95

Val Cys Val Thr Glu Val His Ala Ala Thr Met Asn Ser Asp Met Leu
            100                 105                 110

Arg Asn Trp Val Ala Asp His Pro Ala Ile Ala Glu Gln Leu Leu Arg
            115                 120                 125

Val Leu Ala Arg Arg Leu Arg Arg Thr Asn Ala Ser Leu Ala Asp Leu
        130                 135                 140

Ile Phe Thr Asp Val Pro Gly Arg Val Ala Lys Thr Leu Leu Gln Leu
145                 150                 155                 160

Ala Asn Arg Phe Gly Thr Gln Glu Ala Gly Ala Leu Arg Val Asn His
                165                 170                 175

Asp Leu Thr Gln Glu Glu Ile Ala Gln Leu Val Gly Ala Ser Arg Glu
            180                 185                 190

Thr Val Asn Lys Ala Leu Ala Thr Phe Ala His Arg Gly Trp Ile Arg
            195                 200                 205

Leu Glu Gly Lys Ser Val Leu Ile Val Asp Thr Glu His Leu Ala Arg
210                 215                 220

Arg Ala Arg Val
225

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggaattcga tgtgtgcaga tgaagg                                         26

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cggaattcta ttcgttacct gcaggc                                         26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cggaattcgt ggaaggtgta cagg                                           24
```

```
<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acgcgtcgac tattcgttac ctgcagg                                              27

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggaaaatgca ggcaccgc                                                        18

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gactacctct ggaatctagg                                                      20
```